(12) United States Patent  
Vilser et al.

(10) Patent No.: US 7,677,729 B2  
(45) Date of Patent: Mar. 16, 2010

(54) APPARATUS AND METHOD FOR THE ANALYSIS OF RETINAL VESSELS

(75) Inventors: Walthard Vilser, Rudolstadt (DE); Christine Kassner, Ilmenau (DE)

(73) Assignee: Imedos GmbH, Jena (DE)

( * ) Notice: Subject to any disclaimer, the term of this patent is extended or adjusted under 35 U.S.C. 154(b) by 522 days.

(21) Appl. No.: 11/734,371

(22) Filed: Apr. 12, 2007

(65) Prior Publication Data

US 2007/0244396 A1    Oct. 18, 2007

(30) Foreign Application Priority Data

Apr. 18, 2006    (DE)    .................    10 2006 018 445

(51) Int. Cl.  
    G03B 9/28    (2006.01)  
    G03B 1/48    (2006.01)
(52) U.S. Cl. .................. 351/206; 351/205; 351/221
(58) Field of Classification Search ......... 351/205–206, 351/221; 354/62  
See application file for complete search history.

(56) References Cited

U.S. PATENT DOCUMENTS 5,576,780 A * 11/1996 Yancey ................... 351/211  
6,276,798 B1 * 8/2001 Gil et al. ................ 351/206

2007/0002276 A1 * 1/2007 Hirohara et al. ............. 351/206

FOREIGN PATENT DOCUMENTS

DE    195 48 935    7/1996

OTHER PUBLICATIONS

Ophthalmology, vol. 106, Dec. 1999, pp. 2269-2280, Hubbard et al., Methods for Evaluation of Retinal Microvascular Abnormalities Associated with Hypertension/Sclerosis in the Atherosclerosis Risk in Communities Study.  
The Lancet, vol. 358 (2001), pp. 1134-1140, Wong TY et al. (Retinal microvascular abnormalities and incident stroke: The Atherosclerosis Risk in Communities Studies.  
Current Eye Research, vol. 27 (2003) 143-149, Knudsen MD et al., Revised formulas for summarizing retinal vessel diameters.

* cited by examiner

*Primary Examiner*—Scott J Sugarman  
*Assistant Examiner*—Dawayne A Pinkney  
(74) *Attorney, Agent, or Firm*—Reed Smith LLP

(57) ABSTRACT

The object of an apparatus and a method for the analysis of retinal vessels is to improve the reproducibility of individually determined artery-to-vein ratios and to reduce the measurement uncertainty in determining the artery-to-vein ratio in order to substantially increase the individual validity of the determined values for vessel diagnosis. At least two images are recorded successively as an image sequence in a predetermined timed sequence adapted to the vasomotricity of the vessels and are evaluated such that a mean artery-to-vein ratio is formed from artery-to-vein ratios that are determined on the basis of the at least two images.

25 Claims, 1 Drawing Sheet

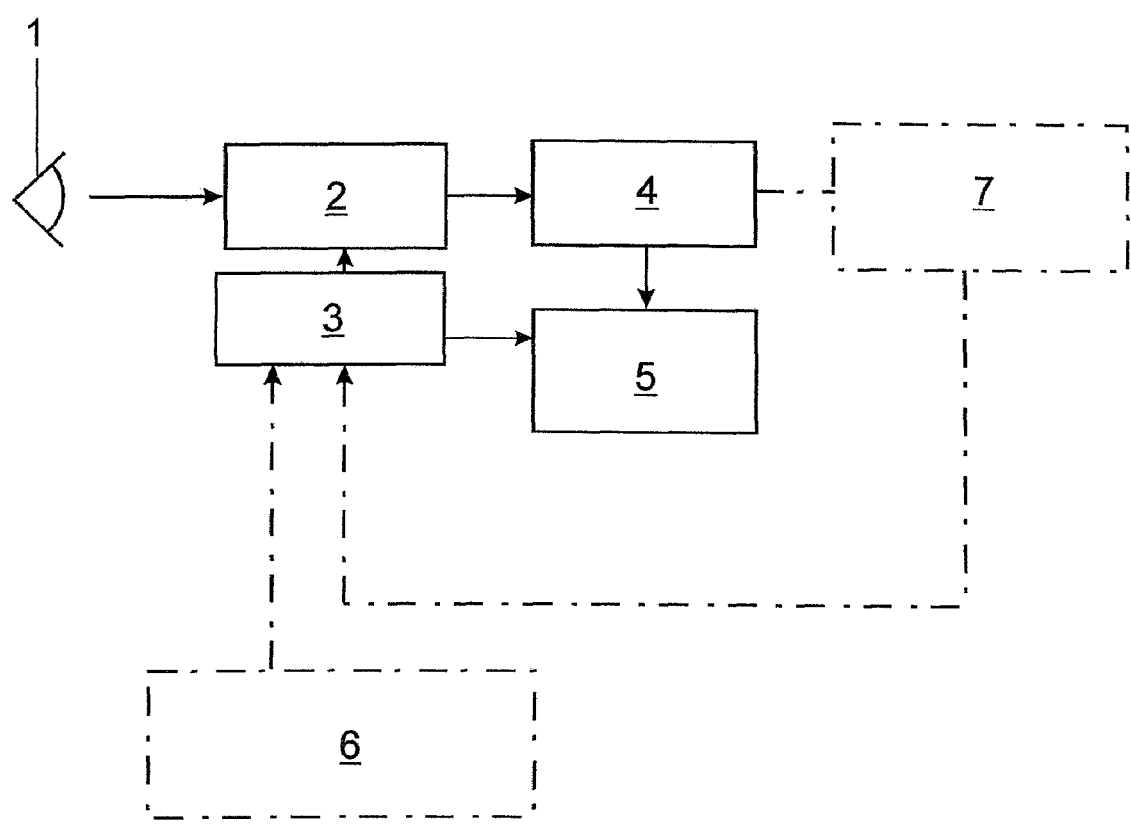

APPARATUS AND METHOD FOR THE ANALYSIS OF RETINAL VESSELS

CROSS-REFERENCE TO RELATED APPLICATIONS

This application claims priority of German Application No. 10 2006 018.445.9, filed Apr. 18, 2006, the complete disclosure of which is hereby incorporated by reference.

BACKGROUND OF THE INVENTION a) Field of the Invention

The invention is directed to an apparatus for the analysis of retinal vessels which contains a retinal camera for recording images of the ocular fundus, at least one image storage, means for detecting arterial and venous vessels in the images, means for determining the vessel diameters of the detected arterial and venous vessels, and means for determining artery-to-vein ratios (AVRs) from the determined vessel diameters.

b) Description of the Related Art

The invention is further directed to a method for the analysis of retinal vessels through the evaluation of digital fundus images in which a ring-shaped measurement zone containing vessel portions which proceed from a central vessel, which are to be distinguished as arteries or veins, and which are to be measured is arranged around the papilla at a distance therefrom, a vessel diameter being determined for each of these vessel portions, wherein a retinal arterial vessel diameter equivalent and a retinal venous vessel diameter equivalent are determined from the determined vessel diameters of the arterial and venous vessel portions, and an artery-to-vein ratio is determined from the vessel diameter equivalents of the arteries and veins.

By means of a quantitative vessel analysis using digital fundus images, it is possible to assess vascular risk which can be determined, e.g., by means of an artery-to-vein ratio (AVR) according to Hubbard et al. (Ophthalmology, Vol. 106, December 1999, pages 2269-2280). For example, in a study (ARIC study) it was possible to determine a relationship between the artery-to-vein ratio and the cardiovascular risk in women and for stroke and diabetes in women and men independent from blood pressure and other risk factors.

Wong T Y et al. (Retinal microvascular abnormalities and incident stroke: The Atherosclerosis Risk in Communities Studies, The Lancet, Vol. 358 (2001), pages 1134-1140) show that risk groups for stroke and other severe vascular diseases can be classified based on the AVR for estimating a systemic microvascular risk.

All of the systems for determining the artery-to-vein ratio have a retinal camera, units for storing the recorded individual image, means for detecting arterial and venous vessels, means for determining vessel diameters, and means for calculating the AVR.

A digital fundus image recorded by the retinal camera is evaluated such that diameters of arteries and veins located within a ring-shaped measurement zone around the papilla are determined according to a standardized protocol and summarized according to a standardized model formula to form a retinal arterial vessel diameter equivalent CAE and a retinal venous vessel diameter equivalent CVE whose quotient (CAE/CVE) gives a value for the AVR. Different model formulas may be applied (Knudsen M D et al., Revised formulas for summarizing retinal vessel diameters, Current Eye Research, Vol. 27 (2003) 143-149).

A procedure of this kind is suitable only for epidemiological studies with a high number of cases (10,000 or more) because systematic error proportions of the individual AVR values are substantially randomized and along with the random errors of the individual AVR values only play a subordinate role for epidemiological studies and evaluations in group averages.

However, the methods are very uncertain and are usable only conditionally for individual diagnoses because, as a result of the random systematic errors which vary between individuals, the scatter of the individual central equivalents and of the artery-to-vein ratios in individual examinations is very high and leads to unsatisfactory reproducibility. Under certain conditions, this scatter can spread over a plurality of risk assessment groups so that the risk classification of a patient can vary between high risk and normal risk in studies that are repeated after short intervals. Therefore, the static vessel analysis can only be used conditionally.

OBJECT AND SUMMARY OF THE INVENTION

Accordingly, it is the primary object of the invention to improve the reproducibility of individually determined artery-to-vein ratios and to reduce the measurement uncertainty in determining the artery-to-vein ratio in order to substantially increase the individual validity of the determined values for vessel diagnosis.

This object is met, according to the invention, by an apparatus for the analysis of retinal vessels of the type mentioned in the beginning in that the retinal camera is connected to an image sequence control unit which carries out a control of the time intervals which is adapted to the period of vasomotor waves and a control of the quantity of images of a sequence of images to be recorded for which an image sequence storage is provided for storing images, and in that the means for determining the artery-to-vein ratio are designed to determine a mean artery-to-vein ratio from artery-to-vein ratios which are determined from at least two images of an image sequence.

In a particularly advantageous further development of the invention, the image sequence control unit is connected to means for determining maxima and minima of the vasomotor waves or of the systoles in the area of the maxima of vasomotor waves or of the diastoles in the area of the minima of vasomotor waves as image recording times which are supplied to the retinal camera by the image sequence control unit for recording images.

Suitable measuring means are, e.g., continuously measuring measurement devices for blood pressure or blood volume (plethysmographic methods) but also methods which determine the maxima or minima of the wave-shaped changes in heart rate, e.g., based on EKG signals. These signals reflect the periods of the vasomotor waves. Means for determining the systolic and diastolic times are sufficiently well known from the prior art.

In another development of the invention, the image sequence control unit is connected to means for the continuous detection of the retinal vessel diameters or of the retinal blood volume, particularly of a retinal artery, and means for determining maxima and minima of vasomotor waves of the vessel diameter or of the retinal blood volume as image recording times which are supplied to the retinal camera by the image sequence control unit for recording images. Means for detecting redness of the papilla for detecting the maxima and minima of vasomotor waves can also by used in an advantageous manner.

It can also be advantageous when the means for determining the artery-to-vein ratio have an image evaluating device by which the recorded images can be validated visually or automatically. Further, it is possible that an image adjustment is carried out by means of an image correction unit for correcting eye movements.

According to a further development of the invention, means are provided for recording video sequences of the ocular fundus in continuous light.

The above-stated object is further met according to the invention by a method for the analysis of retinal vessels of the type mentioned in the beginning in that at least two images, as fundus images to be evaluated, are recorded successively in a timed sequence that is adapted to the period of vasomotor waves as an image sequence, and in that a mean artery-to-vein ratio is formed from artery-to-vein ratios that are determined based on at least two images.

In contrast to known methods, the artery-to-vein ratio is determined by means of at least two images of an image sequence which are not recorded at arbitrary times but in a timed sequence of the image recording which is essential to the invention and which is determined by the vasomotricity of the vessels. The substantial advantage in adapting the timed sequence of image recording to a vasomotor wave, particularly the strongest individual vasomotor wave which is therefore the dominant vasomotor wave, consists in that vasomotor amplitude variations of the vessel diameters which, with period lengths of several seconds, e.g., periods of 10 seconds or 20 seconds in the arteries, are substantially greater than the vasomotor variations occurring in the veins have substantially less influence on the artery-to-vein ratio value as a result of the invention. The vasomotor wave with a period of 10 seconds as one of a plurality of vasomotor waves is usually dominant.

Further, the systematic measurement error of the individual measurement caused by changes in the imaging scale from one recording to another is randomized and substantially reduced by the invention. Above all, this is a matter of reducing the measurement uncertainty in determining the central equivalents.

The image sequences determined by the quantity of images and timed sequences of image recordings can be recorded in different ways for adapting to the vasomotricity of the vessels.

Therefore, in a particular realization of the invention, the image recordings are carried out at fixed time intervals adapted to the average period of the dominant vasomotor wave in that one half of the period length of the dominant vasomotor wave is provided as time interval. The dominant vasomotor wave and its period length can be determined in particular by continuous measurements of blood pressure and heart rate, by recording the arterial and venous vessel diameter, or by recording papillary redness.

In image recordings at fixed time intervals, the times at which recording is carried out are not important because when one half of a period length is used as time interval the value fluctuations are eliminated by averaging so that the resulting vessel diameter values are substantially correct.

Further developments of the method with a fixed time interval can be provided in that at least two images are recorded at identical time intervals of from four to six seconds or an odd multiple of this fixed time interval, or in that at least two images are recorded at identical time intervals of from eight to twelve seconds or at an odd multiple of a fixed time interval of from eight to twelve seconds.

Further, the method according to the invention can be developed in such a way that the image sequence is a digital video recording with a recording duration of at least ten seconds, preferably twenty seconds, with continuous illumination and a video standard of twenty-five frames per second.

In a particularly advantageous manner, the actual period of the vasomotor wave is detected in that times at which vasomotor-dependent vascular changes, changes in blood volume, blood pressure or heart rate take on maximum and minimum values are selected for setting the timed sequence of the image recording.

Therefore, with the method according to the invention, the image recordings can be carried out in a systole of the maximum of vasomotor waves and in a diastole of the minimum of vasomotor waves of the vessel diameter, of the retinal blood volume, or of the blood pressure. But the image recordings can also be carried out in a systole of the minimum of the heart rate of vasomotor waves and in a diastole of the maximum of the heart rate of vasomotor waves.

The images in the image sequence of an unchanged fundus section recorded with identical recording settings of an image recording system can be subjected to a calibration check. An image adjustment can be provided for correcting eye movements.

In a preferred variant of the invention, the following methods steps are provided for image sequence evaluation:

the arterial and venous vessel portions to be measured are selected from a first starting image and the coordinates of the selected vessel portions are stored, the images of the image sequence are adjusted with respect to one another for covering identical vessel portions to be measured, wherein the coordinates of the vessel portions of image sequence recorded successively in time after the starting image are converted to the stored coordinates of the starting image, mean vessel diameters are determined from images for the vessel portions based on the converted coordinates of the vessel portions in the sequence images, the vessel diameter equivalents for the arteries and veins are determined and the artery-to-vein ratio is determined from the vessel diameter equivalents of the arteries and veins based on the images, a mean vessel diameter equivalent for the arteries and a mean vessel diameter equivalent for the veins are determined from the vessel diameter equivalents of the images, and a mean artery-to-vein ratio is determined therefrom, or a mean artery-to-vein ratio is determined from the artery-to-vein ratios that were determined based on the images.

As an alternative to the above-mentioned embodiment, the following method steps can be provided for evaluating the image sequence:

the arterial and venous vessel portions to be measured are selected in each image of the image sequence, mean vessel diameters are determined from images for the vessel portions, the vessel diameter equivalents for the arteries and veins are determined and the artery-to-vein ratio is determined with images from the vessel diameter equivalents of the arteries and veins, a mean vessel diameter equivalent for the arteries and a mean vessel diameter equivalent for the veins are determined from the vessel diameter equivalents of the images, and a mean artery-to-vein ratio is determined therefrom, or a mean artery-to-vein ratio is determined from the artery-to-vein ratios that were determined based on the images.

The invention will be described more fully in the following with reference to embodiment examples in connection with the schematic drawing. The drawing shows an apparatus for retinal vessel analysis in a block diagram.

BRIEF DESCRIPTION OF THE DRAWING

The drawing illustrates the basic operation of the present invention in block diagram form.

DESCRIPTION OF THE PREFERRED EMBODIMENTS

A nonmydriatic or mydriatic retinal camera 2 with digital imaging or a digitizing system for fundus photography is provided for examining the eye 1 of a patient and is connected to an image sequence control unit 3 for controlling the sequence of image recordings of the ocular fundus. The images which are recorded by the method according to the invention are stored at least temporarily with image designation and time of recording in an image sequence storage 4 from which an image sequence evaluating device 5 takes images for evaluation to determine a mean AVR value.

Of course, the apparatus comprises input media and output media for dialog mode and for displaying and outputting results, e.g., a keyboard, mouse, screen and printer, which are not shown in the drawing.

The first embodiment example is directed to the determination of AVR values based on an individual image sequence, by which is meant snapshots of the ocular fundus which are taken at fixed time intervals by the retinal camera 2. For this purpose the image sequence control unit 3 supplies control signals to the retinal camera 2 which correspond to the fixed time intervals.

A mean AVR value corresponding to the method steps described in the following is determined on the basis of the images originating from the image sequence by means of the image sequence evaluating device 5.

The recording of the images of an image sequence is carried out with the same camera settings and on a section of the fundus that is unchanged as far as possible. Because of the control of the recording times by the image sequence control unit 3, a time regime is started by an examining person with the free triggering of the first fundus recording. The further images are triggered in a programmed manner according to this time regime, or the examining person is prompted to trigger the next respective image by a signal, e.g., a beep.

Three additional images are preferably recorded after the starting recording every five seconds so that four images are made over fifteen seconds and are available as an image sequence by way of the image sequence storage 4 for an AVR image sequence evaluation. The apparatus for the analysis of retinal vessels can advantageously also have an imaging system which makes it possible, if required, to archive the AVR values determined according to the invention according to two variants.

First, the images can be subjected to an image assessment visually or automatically for validating them. Images which do not correspond to a given image quality for subsequent evaluation are sorted out or, as the case may be, lead to the rejection of the entire image sequence and to an interruption of the examination.

The first variant provides the following method steps for determining AVR values:
- arterial and venous vessel portions to be measured are determined manually or automatically in a first starting image and the vessel coordinates are stored,
- additional images of the image sequence which are taken from the image sequence storage are oriented one after the other with respect to the starting image so that identical vessel portions to be measured are placed one on top of the other and correspond to the coordinates of the vessel portions in the starting image which are to be measured,
- a mean vessel diameter is determined manually or automatically from images for each vessel portion in that the vessel diameters are measured by segments along identical vessel portions,
- vessel diameter equivalents of the arteries and veins and an AVR value are determined in accordance with the images,
- vessel diameter equivalents CAE, CVE, AVR are determined as mean vessel diameter equivalents for arteries and veins and mean AVR values, and mean AVR values are determined by averaging the vessel diameter equivalents and AVR values from the images.

In addition to or as an alternative to the latter method step, mean vessel diameters can be determined for the vessel portions also by averaging the images of the image sequence and determining therefrom mean equivalents for arteries CAEm and veins CVEm and a mean AVRm value as a quotient of CAEm/CVEm.

The determined values are subsequently logged, stored in a patient-specific manner and suitably outputted.

A second variant differs from the first in that the vessel portions to be measured are determined anew in every image so that vessel portions which need no longer be identical to those of the starting image are included in the determination of a mean AVR value.

The first variant has the advantage that the vessel and vessel type need only be determined once, which is particularly suitable for manual procedures. The second variant, on the other hand, is better for automatic evaluation because errors in determining the vessel portions to be measured have less influence on the overall result and can even be ignored when there are many images.

While the image interval of 5 s is advantageous with a minimum image sequence of 2 images, the time regime can also be an odd multiple of 5 s.

It is essential for the invention to include more than one image in the determination of the AVR value. The image sequence time or fixed timed interval between the images is adapted to the period of vasomotor waves. This adaptation ensures that two successive images always have approximately the same amount of vasomotorial deviation from the actual mean value but with different mathematical signs, so that the mean value calculated from the measurement values gives approximately the actual mean vessel diameter.

The protocol of the prior art used for determining the AVR values, the formula for calculating the vessel diameter equivalents, and the known guidelines applied for determining the vessel portions to be measured are not relevant to the invention.

The manner in which the digital fundus recordings are generated (mydriatic or nonmydriatic retinal camera, laser scanner or other image-generating system in strobe mode or with continuous illumination) or the way in which the images and data are stored in a patient-specific manner are also not relevant.

It is immaterial whether the image sequence is generated by a digital or an analog photographic or video camera so long as the images are ultimately stored in the image sequence storage 4 in digitized form by a framegrabber or scanner. However, the fundus recordings are preferably produced in strobe mode in the first embodiment example.

According to a second embodiment example, the determination of the AVR value is carried out based on a "continuous"

image sequence as is preferably the case in a video image sequence with many images and defined time intervals.

In contrast to known technical solutions which evaluate exclusively recordings made in strobe operation, the image sequence control unit 3 supplies a starting signal and an end signal to the retinal camera 2 that has been modified for digital video recording for recording the video image sequence preferably with continuous illumination. The digital video image sequence is stored at least temporarily in the image sequence storage 4 and the image designations together with the times of the recording are sent to the image sequence evaluation device 5 for determining a mean AVR value.

The mean central equivalents and a mean AVR value are determined by way of all of the video images corresponding to the method steps of the first embodiment example by means of the image sequence evaluating device 5. The central equivalents and the AV value of the images of the video image sequence can be outputted graphically as a function of time and can supply information about the time variability in addition to the mean values which are calculated over time.

In this embodiment example, it is again essential for the invention that more than one image is included in the evaluation, wherein the error influences of the vasomotor waves are eliminated by averaging.

A third embodiment example provides an individual image sequence as in the first embodiment example, but the recording times of the images are determined by additional measurement devices 6 or 7 shown in dashed lines in the drawing.

The measuring device 6 serves to determine a systolic time in the maximum of the vasomotor blood pressure waves or a diastolic time in the vasomotor minimum. For the embodiment example, the measuring device 6 carries out a continuous blood pressure measurement, and means are provided for detecting the above-mentioned maxima and minima which are conveyed to the image sequence control unit 3 as times for making the fundus recordings.

In another procedure, the individual period lengths of the dominant vasomotor wave, instead of the recording times, are determined from the continuous blood pressure values by the measuring device 6 and are conveyed to the image sequence control unit 3.

Measuring device 7 is designed for determining the systolic maximum in the region of the maximum of the dominant vasomotor wave or the diastolic minimum in the region of the minima of the dominant vasomotor wave as triggering times for the fundus recordings to be evaluated or for determining the individual period length of the dominant vasomotor wave directly at the retinal vessels. The measuring device 7 can be constructed as a measuring device for recording the arterial or venous vessel diameter according to DE 195 48 935 A1 or for continuous recording of papillary redness (representative of the blood volume), wherein the determination of the times or the period lengths is carried out with means known per se.

The times determined by the two measuring devices 6, 7 are sent to the image sequence control unit 3 for generating control signals which trigger the recordings by the retinal camera 2.

In procedures of this kind, it is sufficient when the image sequence is limited to two images, one in the maximum and one in the minimum. The advantage consists in an individually exact determination of the time interval between the image recordings.

In case the individual period length of the dominant vasomotor wave has been determined, the examining person can trigger the starting recording himself/herself, while one half of the period length or the odd multiple of one half of the period length is given as a fixed time interval between the images.

While the foregoing description and drawings represent the present invention, it will be obvious to those skilled in the art that various changes may be made therein without departing from the true spirit and scope of the present invention.

What is claimed is:

1. An apparatus for the analysis of retinal vessels comprising:
    a retinal camera for recording images of the ocular fundus;
    at least one image storage;
    means for detecting arterial and venous vessels in the images;
    means for determining the vessel diameters of the detected arterial and venous vessels;
    means for determining artery-to-vein ratios from the determined vessel diameters;
    said retinal camera being connected to an image sequence control unit which carries out a control of the time intervals or times which is adapted to the period of vasomotor waves and a control of the quantity of images of a sequence of images to be recorded for which an image sequence storage is provided for storing images; and
    said means for determining artery-to-vein ratios being designed to determine a mean artery-to-vein ratio from artery-to-vein ratios which are determined from at least two images of an image sequence.

2. The apparatus according to claim 1, wherein the image sequence control unit is connected to means for determining maxima and minima of the vasomotor waves as image recording times which are supplied to the retinal camera by the image sequence control unit for recording images.

3. The apparatus according to claim 2, wherein the means for determining the maximum and minimum of vasomotor blood pressure waves comprise measuring devices for the continuous measurement of blood pressure or blood volume or heart rate.

4. The apparatus according to claim 1, wherein the image sequence control unit is connected to means for the continuous detection of the retinal vessel diameters or of the retinal blood volume and for determining maxima and minima of vasomotor waves of the vessel diameter or of the retinal blood volume as image recording times which are supplied to the retinal camera by the image sequence control unit for recording images.

5. The apparatus according to claim 4, wherein the image sequence control unit is connected to means for the continuous detection of the vessel diameter of a retinal artery.

6. The apparatus according to claim 1, wherein the means for determining the arterial central equivalent and the venous central equivalent and for determining the artery-to-vein ratio have an image evaluating device.

7. The apparatus according to claim 1, wherein an image correction unit is provided for real-time correction of the images.

8. The apparatus according to claim 1, wherein means are provided for recording video sequences of the ocular fundus in continuous light.

9. A method for the analysis of retinal vessels comprising the steps of:
    evaluating digital fundus images in which a ring-shaped measurement zone containing vessel portions which proceed from a central vessel, which are to be distinguished as arteries or veins, and which are to be measured;

arranging said measurement zone around the papilla at a distance therefrom;

determining a vessel diameter for each of these vessel portions;

determining a retinal arterial vessel diameter equivalent and a retinal venous vessel diameter equivalent from the determined vessel diameters of the arterial and venous vessel portions;

determining an artery-to-vein ratio is determined from the vessel diameter equivalents of the arteries and veins;

recording at least two images, as fundus images to be evaluated, successively in a timed sequence that is adapted to the period of vasomotor waves as an image sequence; and forming a mean artery-to-vein ratio from artery-to-vein ratios that are determined based on the at least two images.

10. The method according to claim 9, wherein the at least two images are recorded at a fixed time interval corresponding to one half of the period length of the dominant vasomotor wave.

11. The method according to claim 10, wherein the dominant vasomotor wave and the period length of the wave are determined by measurement of blood pressure, by recording the arterial or venous vessel diameter, by recording the retinal or ocular blood volume, or by recording papillary redness.

12. The method according to claim 9, wherein at least two images are recorded at identical time intervals of four to six seconds.

13. The method according to claim 9, wherein at least two images are recorded at identical time intervals amounting to an odd multiple of a fixed time interval of four to six seconds.

14. The method according to claim 9, wherein at least four images are recorded at identical time intervals of four to six seconds or of an odd multiple thereof.

15. The method according to claim 9, wherein at least two images are recorded at identical time intervals of eight to twelve seconds or at an odd multiple of a fixed time interval of eight to twelve seconds.

16. The method according to claim 9, wherein a video image sequence is recorded and digitally stored.

17. The method according to claim 16, wherein the image sequence is a digital video recording with a recording duration of at least ten seconds.

18. The method according to claim 16, wherein the image sequence is a digital video recording with a recording duration of at least twenty seconds.

19. The method according to claim 9, wherein the image recordings are carried out at times at which vasomotor-dependent changes in vessel diameter, or in blood volume, or in blood pressure, or in heart rate take on maximum or minimum values.

20. The method according to claim 19, wherein the image recordings are carried out in a systole of the minimum of vasomotor waves and in a diastole of the maximum of vasomotor waves of the vessel diameter or retinal blood volume or blood pressure.

21. The method according to claim 19, wherein the image recordings are carried out in a systole of the minimum of the heart rate of vasomotor waves and in a diastole of the maximum of the heart rate of vasomotor waves.

22. The method according to claim 9, further comprising the following additional methods steps:

selecting the arterial and venous vessel portions to be measured from a first starting image and the coordinates of the selected vessel portions are stored;

adjusting the images of the image sequence with respect to one another for covering identical vessel portions to be measured, wherein the coordinates of the vessel portions of sequence images recorded successively in time after the starting image are converted to the stored coordinates of the starting image;

determining mean vessel diameters from images for the vessel portions based on the converted coordinates of the vessel portions in the sequence images, determining the vessel diameter equivalents for the arteries and veins and the artery-to-vein ratio from the vessel diameter equivalents of the arteries and veins based on the images; and determining a mean vessel diameter equivalent for the arteries and a mean vessel diameter equivalent for the veins from the vessel diameter equivalents of the images, and a mean artery-to-vein ratio therefrom, or calculating a mean artery-to-vein ratio from the individual artery-to-vein ratios of the images.

23. The method according to claim 9, further comprising the following additional method steps:

selecting the arterial and venous vessel portions to be measured in each image;

determining mean vessel diameters from images for the vessel portions;

based on images, determining the vessel diameter equivalents for the arteries and veins the artery-to-vein ratio from the vessel diameter equivalents of the arteries and veins; and determining a mean vessel diameter equivalent for the arteries and a mean vessel diameter equivalent for the veins from the vessel diameter equivalents of the images, and a mean artery-to-vein ratio therefrom, or calculating a mean artery-to-vein ratio from the individual artery-to-vein ratios of the images.

24. The method according to claim 22, wherein the images in the image sequence are of an unchanged fundus section and are recorded with identical recording settings of an image recording system.

25. The method according to claim 24, wherein the images of the image sequence are subjected to a calibration check.

* * * * *